United States Patent [19]

Tkatchouk et al.

[11] Patent Number: 5,383,448
[45] Date of Patent: Jan. 24, 1995

[54] APPARATUS FOR PRODUCING A HYPOXIC GASEOUS MIXTURE USING HOLLOW FIBERS OF POLY-4-METHYL-PENTHENE-1

[75] Inventors: Elena N. Tkatchouk; Tatiana N. Tsyganova, both of Moscow; Regula Staebler, Vernier, Switzerland

[73] Assignee: Tradotec, S.A., Vernier, Switzerland

[21] Appl. No.: 56,679

[22] Filed: May 3, 1993

Related U.S. Application Data

[62] Division of Ser. No. 898,072, Jun. 12, 1992, Pat. No. 5,207,623.

[30] Foreign Application Priority Data

Jun. 12, 1991 [EP] European Pat. Off. ........ 91810445.6

[51] Int. Cl.⁶ .............. A62B 7/10; A62B 23/02; B01D 53/22; G05B 1/00
[52] U.S. Cl. ............... 128/205.11; 128/205.12; 128/205.27; 128/200.24; 128/203.12; 95/54
[58] Field of Search .............. 128/200.24, 205.11, 128/205.12, 205.27, 204.13, 202.12, 202.13, 202.16, 204.18, 203.25, 203.12; 95/54

[56] References Cited

U.S. PATENT DOCUMENTS

| | | | |
|---|---|---|---|
| 3,674,022 | 7/1972 | Dounoucos | 128/205.27 |
| 4,421,529 | 12/1983 | Revak et al. | 95/54 |
| 4,781,907 | 11/1988 | McNeill | 95/54 |
| 4,844,059 | 7/1989 | Koch | 128/205.27 |
| 4,894,068 | 1/1990 | Rice | 95/54 |
| 5,101,819 | 4/1992 | Lane | 128/204.18 |
| 5,248,319 | 9/1993 | Ekiner et al. | 95/54 |

FOREIGN PATENT DOCUMENTS

| | | | |
|---|---|---|---|
| 2524239 | 1/1976 | Germany | 128/205.27 |
| 0087020 | 5/1984 | Japan | 128/205.27 |
| 2053693 | 2/1981 | United Kingdom | 128/204.13 |
| 2053694 | 2/1981 | United Kingdom | 128/204.13 |
| 2053695 | 2/1981 | United Kingdom | 128/204.13 |

*Primary Examiner*—Kimberly L. Asher
*Attorney, Agent, or Firm*—Emmanuel Lobata

[57] ABSTRACT

Apparatus for producing a hypoxic gas mixture having a higher nitrogen-to-oxygen ratio than atmospheric air has a diaphragm compressor feeding air under pressure to an oxygen-depleting unit having a perforate tube extending axially of a cylindrical chamber having an outlet in one side. The annular space between the perforate tube and the wall of the chamber is filled with axially extending hollow fibers of poly-4-methyl-penthene-1. Ends of the chamber are closed except for the interiors of the hollow fibers which are open to the atmosphere. The walls of the hollow fibers are more permeable to oxygen than to nitrogen so that part of the oxygen escapes through open ends of the hollow fibers, thereby increasing the nitrogen-to-oxygen content of the gas.

3 Claims, 2 Drawing Sheets

APPARATUS FOR PRODUCING A HYPOXIC GASEOUS MIXTURE USING HOLLOW FIBERS OF POLY-4-METHYL-PENTHENE-1

REFERENCE TO PRIOR APPLICATION

This application is a division of application Ser. No. 07/898,072, filed Jun. 12, 1992, now U.S. Pat. No. 5,207,623.

FIELD OF INVENTION

The invention relates to apparatus for producing a hypoxic gaseous mixture, namely, a gaseous mixture composed of nitrogen and oxygen, in proportions ranging between 92% and 82% nitrogen and 8% to 18% oxygen by volume.

BACKGROUND OF INVENTION

Hypoxic gaseous mixtures, which will hereinafter be referred to for simplicity as "hypoxic gases," are used in medicine and in the chemical industry. It is known to provide a process for obtaining a hypoxic gas in which highly purified nitrogen, compressed up to 120 to 150 atm, is mixed with air in an injector. The oxygen content of the hypoxic gas obtained by this process ranges between 10% to 13% by volume.

For the reduction of this process to practice, there is known apparatus having a bag of nitrogen gas compressed to 120–150 atm, an ejector for mixing oxygen with the compressed nitrogen, pressure reducing gear for reducing the mixture pressure to 4 atm and a rotometer connected to the patient's mask.

The main drawbacks of this apparatus are as follows.

(a) The low quality of the hypoxic gas thus obtained and the variation of its concentration with time, (b) The potentially high-risk danger from the gas bag at a pressure of 120 to 150 atm.

SUMMARY OF THE INVENTION

It is an object of the present invention to eliminate the above-noted drawbacks of known apparatus and to improve the quality of the hypoxic gas obtained.

The apparatus in accordance with the invention makes it possible substantially to improve the quality of the hypoxic gas produced and, particularly, to increase the stability of its oxygen concentration and to extend the limits of this concentration. Moreover, the apparatus in accordance with the present invention practically eliminates contaminants and provides safety of operation by eliminating very high gas pressure.

In accordance with the invention atmospheric air containing 21% of oxygen and 78% of nitrogen by volume is compressed to a pressure of about 2 atmospheres by a membrane compressor, and is then passed through an oxygen-depleting unit comprising hollow fibers which are more permeable to oxygen than to nitrogen so as to allow a portion of the oxygen to escape to the atmosphere and thereby increase the ratio of nitrogen to oxygen to produce a hypoxic gas. The hypoxic gas is filtered, humidified and conducted to a receptor and/or to a mask for administration to a patient.

BRIEF DESCRIPTION OF DRAWINGS

The invention will be more fully understood from the following description of a preferred embodiment, which is illustrated schematically and by way of example in the accompanying drawings in which.

DESCRIPTION OF PREFERRED EMBODIMENTS

Figure 1:
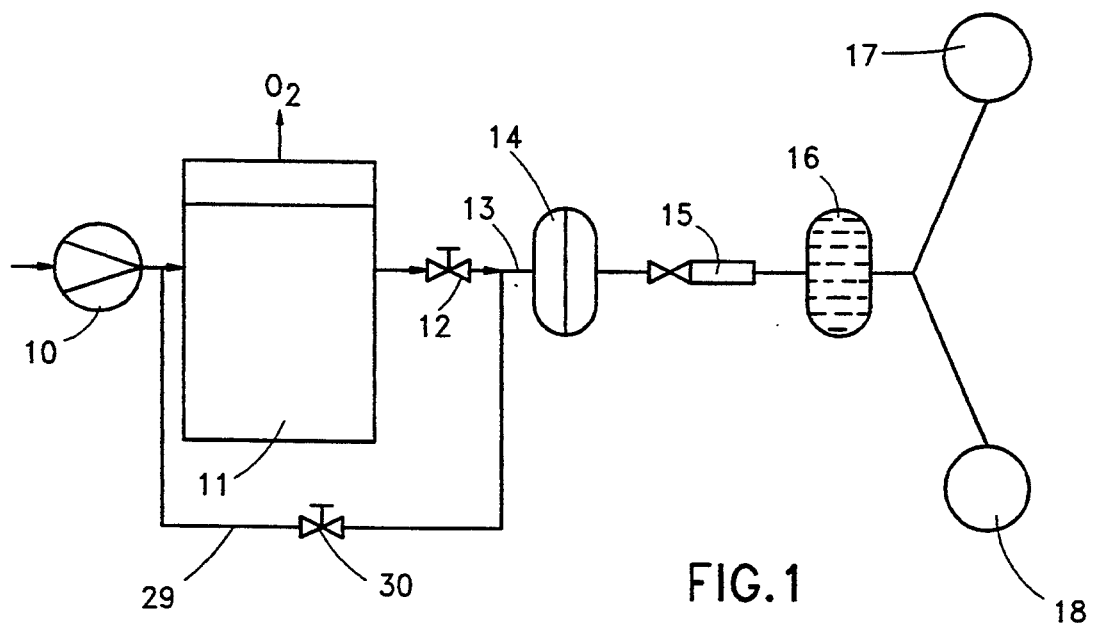
FIG. 1 is a block diagram of a hypoxic gas generator in accordance with the invention.
Figure 5:
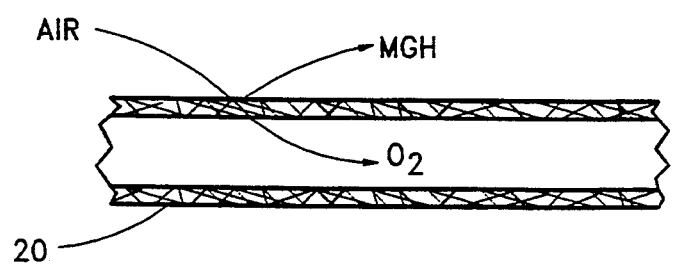
FIG. 5 is an enlarged fragmentary longitudinal section of a fiber of the oxygen-depleting unit.
Figure 6:
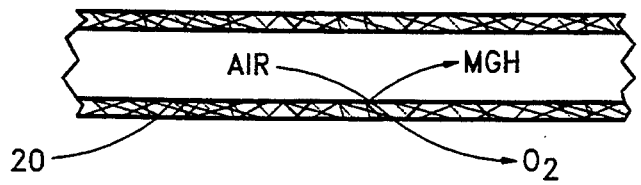
FIG. 6 is a view like FIG. 5, but showing a variation.
Figure 2:
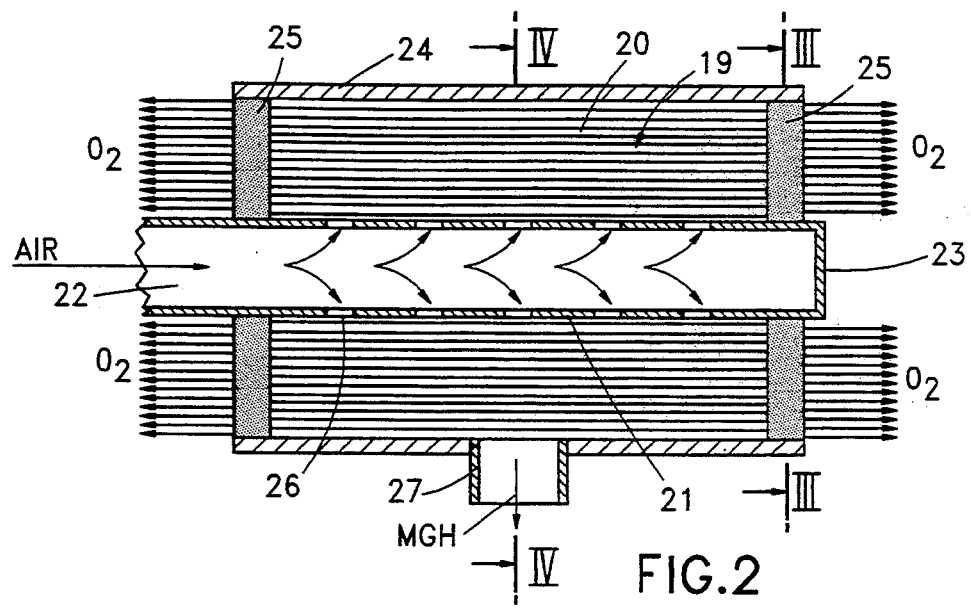
FIG. 2 is an axial section of an oxygen-depleting unit of the hypoxic gas generator.
Figure 3:
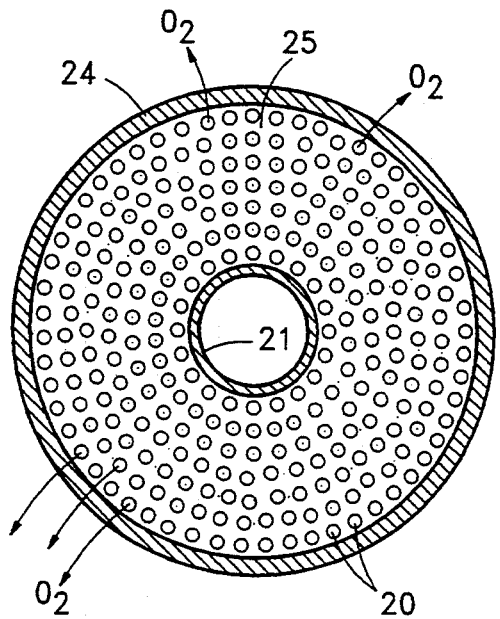
FIG. 3 is a cross section taken on the line III—III in FIG. 2.
Figure 4:
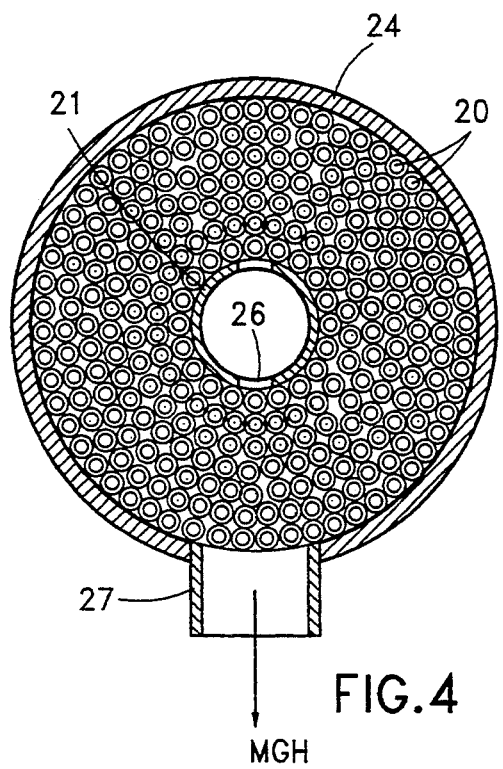
FIG. 4 is a cross section taken on the line IV—IV in FIG. 2.

As shown schematically in the block diagram of FIG. 1, apparatus for producing a hypoxic gas in accordance with the invention comprises an air-compressor 10 which compresses atmospheric air and supplies the compressed air to an oxygen-depleting unit 11 where a portion of the oxygen is removed so as to produce a hypoxic gas having a higher nitrogen-oxygen ratio than atmospheric air.

The resulting hypoxic gas is fed through a control valve 12 to a filter 14 for removing any contaminants in the gas. From the filter 14 the gas flows through a rotameter 15 and a gas mixture humidifier 16 to a receptor 17 and/or a mask 18 for a patient.

The oxygen-depleting unit 11 and control valve 12 are bypassed by a bypass line 29 in which there is a control valve 30. By closing the control valve 12 and opening the control valve 30, air can be supplied intermittently to a patient wearing the mask 18.

The air compressor is a membrane compressor, which compresses atmospheric air to a pressure of the order of two or three atmospheres.

The oxygen-depleting unit 11 (FIGS. 2–6) comprises a bundle 19 of hollow polymeric fibers 20 based on 4-methyl-penthene-1 having a wall thickness of 12–13 microns and an internal diameter of 8–20 microns. The bundle 19 extends longitudinally between a tube 21 of which one end 22 is open and the other end 23 is closed and an impervious cylindrical case 24, which is open at both ends.

Material 25 impregnating the exterior surfaces of the hollow fibers 20 at the two ends of the bundle 19 seals the interstices between the hollow fibers. Thus, the opposite ends of the case 24 are closed except for the interiors of the hollow fibers 20 which are open to the atmosphere. The open end 22 of the tube 21 is connected with the output of the compressor 10. The tube 21 has longitudinally spaced openings 26, and the cylindrical case 24 has, at one side, an orifice 27 which puts the space containing the fibers into communication with the control valve 12.

The air which the compressor 18 forces into the unit 11 through the open end 22 of the tube 21 passes out through the openings 26 and penetrates the bundle 19 where it enters into contact with the fibers 20. Under the action of the pressure prevailing in the interior of the cylindrical case 24, the oxygen and the nitrogen of the air pass through the micropores of the walls of the hollow fibers 20 in a selective manner, the selectivity being explained by the chemical qualities of the hollow fibers (see FIG. 5) in the manner that the flow of compressed air entering the unit 12 is divided in the bundle 19 into a flow of oxygen which flows to the interior of the fibers 20 and is evacuated through the open ends of the fibers at the ends of the cylindrical case 24, and a flow of a hypoxic-mixture (MGH) which passes out through the orifice 27 in tube 22 and hence through the control valve 12 to the filter 14, rotameter 15, humidifier 16, to the receptor 17 and/or a mask 18 for a patient.

The filter 14 is a cloth filter made up of polymeric fine fiber material which is manufactured from polymers such as polyvinilidenaphthalid, fluorplast, polyvinilchloride, etc. by an electrostatic molding method and is known commercially as Petryanov filter cloth.

The filter is made up of one or many layers of the cloth and removes contaminants from the gas.

The rotameter 15 is a meter which measures the rate of flow of the hypoxic gas mixture passing through it to the mask 18 and/or the receptor 17.

The humidifier 16 is a vessel containing distilled water through which the hypoxic gas passes and is thereby humidified.

The receiver 17 is a vessel which receives and stores hypoxic gas which is not currently utilized by the mask 18.

What I claim is:

1. Apparatus for producing a hypoxic gaseous mixture comprising:
   means for compressing air;
   an oxygen-depleting means for removing a portion of oxygen from compressed air produced by said compressing means to produce a hypoxic gas, said oxygen-depleting means comprising an elongate chamber having a first end and a second end, an inlet at said first end, a side outlet, a tube having perforations extending longitudinally of said chamber and communicating with said inlet, a multiplicity of hollow fibers extending longitudinally of said chamber, means for closing said first and second ends of said chamber, means for directing air compressed by said air compressing means into said oxygen-depleting means through said inlet, said compressed air flowing through said inlet, into said tube, and communicating with said hollow fibers through said perforations in said tube, a portion of the oxygen in said compressed air flowing through said perforations and said hollow fibers to the surrounding environment, and leaving hypoxic gas in said tube and chamber, said hypoxic gas flowing out of said oxygen-depleting means through said outlet;
   wherein said hollow fibers are more permeable to oxygen than to nitrogen and are made of poly-4-methyl-penthene-1;
   means for filtering hypoxic gas produced by said oxygen-depleting means;
   means for humidifying hypoxic gas produced by said oxygen-depleting means;
   means for delivering hypoxic gas to a patient;
   said apparatus further comprising means for alternating delivery of said hypoxic gas and said compressed air to a patient comprising a bypass line connected to said means for directing said compressed air and in parallel to said oxygen-depleting means, said bypass line connected to said outlet of said oxygen-depleting means, said means for alternating delivery of said hypoxic gas and said compressed air including a first valve in said bypass line for controlling flow of compressed air, and a second valve connected to said outlet of said oxygen-depleting means.

2. Apparatus according to claim 1, in which said hollow fibers have a wall thickness of 12 to 30 microns and an internal diameter of 8 to 20 microns.

3. Apparatus according to claim 1, in which said filter means comprises Petryanov cloth through which said hypoxic gas flows.

* * * * *